United States Patent
Venkatachalam et al.

(10) Patent No.: US 8,538,501 B2
(45) Date of Patent: Sep. 17, 2013

(54) MAPPING AND ABLATION CATHETER SYSTEM

(75) Inventors: Kalpathi Venkatachalam, Jacksonville Beach, FL (US); Samuel J. Asirvatham, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 375 days.

(21) Appl. No.: 12/812,097

(22) PCT Filed: Jan. 9, 2009

(86) PCT No.: PCT/US2009/030548
§ 371 (c)(1),
(2), (4) Date: Nov. 4, 2010

(87) PCT Pub. No.: WO2009/089415
PCT Pub. Date: Jul. 16, 2009

(65) Prior Publication Data
US 2011/0190756 A1   Aug. 4, 2011

Related U.S. Application Data

(60) Provisional application No. 61/010,519, filed on Jan. 9, 2008.

(51) Int. Cl.
*A61B 5/042* (2006.01)
*A61B 18/14* (2006.01)

(52) U.S. Cl.
USPC .......................................... 600/374; 606/41

(58) Field of Classification Search
USPC .......................................... 600/374; 606/41
See application file for complete search history.

(56) References Cited

U.S. PATENT DOCUMENTS

| | | | |
|---|---|---|---|
| 4,945,912 A | 8/1990 | Langberg | |
| 5,454,370 A | 10/1995 | Avitall | |
| 6,088,610 A * | 7/2000 | Littmann et al. | 600/381 |
| 6,210,407 B1 * | 4/2001 | Webster | 606/41 |
| 6,771,996 B2 * | 8/2004 | Bowe et al. | 600/374 |
| 6,939,345 B2 | 9/2005 | KenKnight et al. | |
| 7,039,450 B2 * | 5/2006 | Duarte | 600/374 |
| 7,846,157 B2 * | 12/2010 | Kozel | 606/41 |
| 7,881,809 B2 * | 2/2011 | Rashidi | 607/122 |
| 2005/0256521 A1 | 11/2005 | Kozel | |
| 2006/0089637 A1 | 4/2006 | Werneth et al. | |

OTHER PUBLICATIONS

International Search Report issued by the Korean Patent Office as the International Search Authority on May 18, 2009 Patent Application No. PCT/US2009/030548, filed Jan. 9, 2009; 3 pgs.

International Preliminary Report on Patentability issued by the International Bureau of WIPO on Jul. 13, 2010, Patent Application No. PCT/US2009/030548, filed Jan. 9, 2009; 6 pgs.

* cited by examiner

*Primary Examiner* — Lee S Cohen
(74) *Attorney, Agent, or Firm* — Mueting, Raasch & Gebhardt, P.A.

(57) ABSTRACT

A mapping and ablation catheter system including a radio frequency ablation source having an output, a mapping device, a catheter, and two or more capacitive components. The catheter may include two or more catheter electrodes, wherein two of the two or more catheter electrodes may be electrically coupled to the mapping device. Each of the two or more catheter electrodes may be electrically coupled to a capacitive component, wherein each capacitive component may be electrically coupled to the output of the radio frequency ablation source such that energy delivered to each catheter electrode of the two or more catheter electrodes passes through the capacitive component.

26 Claims, 4 Drawing Sheets

MAPPING AND ABLATION CATHETER SYSTEM

RELATED APPLICATION

The present application is a U.S. National Stage Application of International Application No. PCT/US2009/030548, titled MAPPING AND ABLATION CATHETER SYSTEM, filed on Jan. 9, 2009, published in the English language on Jul. 16, 2009 as International Publication No. WO 2009/089415 A1, which claims the benefit under 35 U.S.C. §119(e) of U.S. Provisional Patent Application No. 61/010,519, filed on Jan. 9, 2008, titled MAPPING AND ABLATION CATHETER SYSTEM, both of which are hereby incorporated by reference in their entirety.

The present invention relates generally to cardiac mapping and ablation catheter systems.

The systems described herein may be used in the mapping and ablation of tissue associated with tachyarrhythmia. In some embodiments, the systems include a catheter that may include one or more electrodes located about the distal end of the catheter. The catheter may be manipulated within one or more cardiac chambers to obtain electrograms from the one or more electrodes. The electrograms may be used to create a map of the cardiac chamber (e.g., the map could be a real electro-anatomic map or an abstract map based on various voltages, timings, and morphologies recorded using the catheter).

Once a selected site that may include arrhythmogenic tissue is identified as a result of the mapping process, radio frequency (RF) energy may be delivered to the same one or more electrodes located about the distal end of the catheter to ablate tissue at the selected site.

The requirements of an ideal mapping electrode, however, are different from those of an ideal ablation electrode. For example, the ideal mapping electrode is typically smaller so as to sample electrograms from very close to the point of contact of the electrode while reducing the effect of "far-field" potentials that are a few millimeters away from the point of contact. In contrast, ablation electrodes are typically larger (in diameter and/or in length) so as to be able to deliver sufficient energy to ablate tissue effectively.

When a small (e.g., short in length) electrode tip is used to ablate tissue, tissue temperature can rise very quickly, but too little power may be delivered to the tissue to effectively produce a lesion. Known non-irrigated ablation catheters have tip electrodes that are 4 millimeters (mm), 5 mm, or 8 mm long. Most commonly, the 5 mm tip is used but occasionally the 8 mm tip is needed (requiring a cumbersome and expensive catheter change) when the 5 mm tip is not sufficient. Mapping with the 8 mm tip is less precise than with the 5 mm tip because large-amplitude far-field signals may be received by the "antenna-effect" of the 8 mm tip, thereby reducing the precision of the mapping process.

Mapping and ablation catheter systems have been previously been described. For example, U.S. Pat. No. 5,454,370, issued 3 Oct. 1995 to Avitall and entitled "Mapping and Ablation Electrode Configuration," describes a mapping/ablation electrode arrangement that provides for flexible lesion size yet maintains discrete localized mapping ability and/or enables the operator to adjust the lesion size (width, length, and depth).

SUMMARY

The present disclosure describes a variety of cardiac mapping and ablation catheter systems that may include a radio frequency ablation source, a mapping device, one or more electrodes, capacitive components located between the catheter electrodes that may be electrically coupled to the mapping device. Each of the electrodes may be electrically coupled to a capacitive component, wherein each capacitive component may be electrically coupled to the output of the radio frequency ablation source such that energy delivered to each catheter electrode of the one or more electrodes passes through the capacitive component.

In some embodiments, the cardiac mapping and ablation catheter system may include a radio frequency ablation source having an output; a mapping device; a catheter having two or more catheter electrodes, wherein two of the two or more catheter electrodes are electrically coupled to the mapping device; and two or more capacitive components, wherein each of the two or more catheter electrodes is electrically coupled to a capacitive component, wherein each capacitive component is electrically coupled to the output of the radio frequency ablation source such that energy delivered to each catheter electrode of the two or more catheter electrodes passes through the capacitive component.

In some embodiments, the cardiac mapping and ablation catheter system may include a radio frequency ablation source having an output; a mapping device; a catheter including a catheter electrode, wherein the catheter electrode is electrically coupled to the mapping device; and a capacitive component, wherein the catheter electrode is electrically coupled to the capacitive component, wherein the capacitive component is electrically coupled to the output of the radio frequency ablation source such that energy delivered to the catheter electrode passes through the capacitive component, and wherein the capacitive component electrically isolates the radio frequency ablation source from the catheter electrodes when the radio frequency ablation source is disabled; a sheath capable of partially surrounding the catheter and sliding along the catheter to selectively expose the catheter electrode; and a sheath electrode located on an exterior surface of the sheath, wherein the sheath electrode is electrically coupled to the mapping device.

In various embodiments, one or more of the following features may be included in the systems of the present disclosure: a sheath capable of partially surrounding the catheter and sliding along the catheter to selectively expose one or more of the two or more catheter electrodes (the sheath may include one or more sheath electrodes located on an exterior surface of the sheath, wherein the one or more sheath electrodes are electrically coupled to the mapping device); a return electrode electrically coupled to the radio frequency ablation source; the capacitive components electrically may isolate the radio frequency ablation source from the two or more catheter electrodes when the radio frequency ablation source is disabled; the capacitance of each capacitive component is 0.001 microfarads to 0.1 microfarads; the radio frequency ablation source is capable of outputting electromagnetic energy at a frequency of about 300 kilohertz or higher; the mapping device is capable of sensing electromagnetic energy in the frequency of about 500 hertz or lower; each of the two or more catheter electrodes is 0.5 millimeters long to 4 millimeters long; the two or more catheter electrodes are spaced apart from each other by 0.5 millimeters to 1 millimeter; a portion of the catheter is flexible; the catheter is flexible; one of the two or more catheter electrodes is located on a distal end of the catheter; etc.

DETAILED DESCRIPTION OF EXEMPLARY EMBODIMENTS

Figure 1:
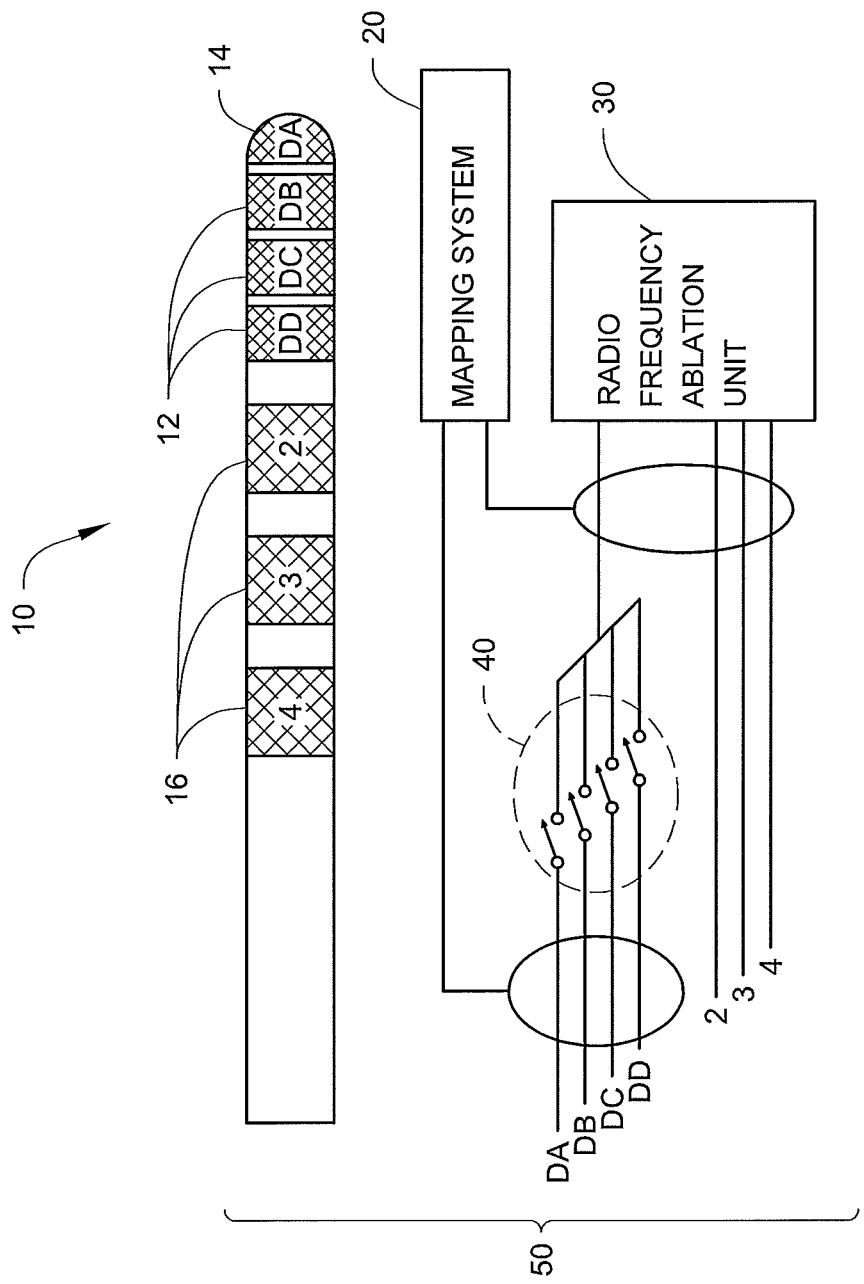
FIG. 1 depicts a schematic diagram of one exemplary embodiment of a mapping and ablation catheter system as described herein.

In the following detailed description of illustrative embodiments of the systems, reference is made to the accompanying figures of the drawing which form a part hereof, and in which are shown, by way of illustration, specific embodiments in which the systems may be provided. It is to be understood that other embodiments may be utilized and structural changes may be made without departing from the scope of the present disclosure.

The words "preferred" and "preferably" as used herein refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments.

As used herein, "a," "an," "the," "at least one," and "one or more" are used interchangeably. The term "and/or" (if used) means one or all of the identified elements/features or a combination of any two or more of the identified elements/features.

The term "and/or" as used herein means one or all of the listed elements/features or a combination of any two or more of the listed elements/features.

FIG. 1 depicts a schematic diagram of one exemplary embodiment of a mapping and ablation catheter system 50. The system may include a catheter 10, a mapping system 20, a radio frequency ablation unit 30, and switches 40. The catheter 10, a portion of catheter 10, or multiple portions of catheter 10 may be flexible.

The catheter 10 may include distal electrodes 12 (e.g., DD, DC, DB), distal tip electrode 14 (e.g., DA), and electrodes 16 (e.g., 4, 3, 2). Each of the electrodes may be electrically coupled to the mapping system 20 and/or radio frequency ablation unit 30. For example, a wire may electrically couple each electrode 12, 14, 16 to the mapping system 20 and/or radio frequency unit 30.

In this embodiment, the connection between the each of the distal electrodes 12/distal tip electrode 14 and the radio frequency ablation unit 30 includes a switch 40. The switches 40 may allow the distal electrodes 12, 14 to be switched into the circuit during ablation operation while only distal electrode 14 may be used during mapping operation. The other electrodes 16 may be activated during a mapping operation also. The switches 40 may, e.g., be electronically-controlled switches. In addition, the switches may be provided using hardware, software, or combinations thereof.

For example, if an operator initially begins an ablation with two distal electrodes creating, e.g., a 4 millimeter (mm) effective tip and not enough power is being delivered to obtain a desired temperature, additional electrodes (e.g., electrodes DC and DD of electrodes 12) may be dynamically "switched-in" to change the impedance/power transfer characteristics of the system. Further, for example, an operator could switch back-and-forth between mapping operation and ablation operation to check for efficacy of ablation.

Figure 2:
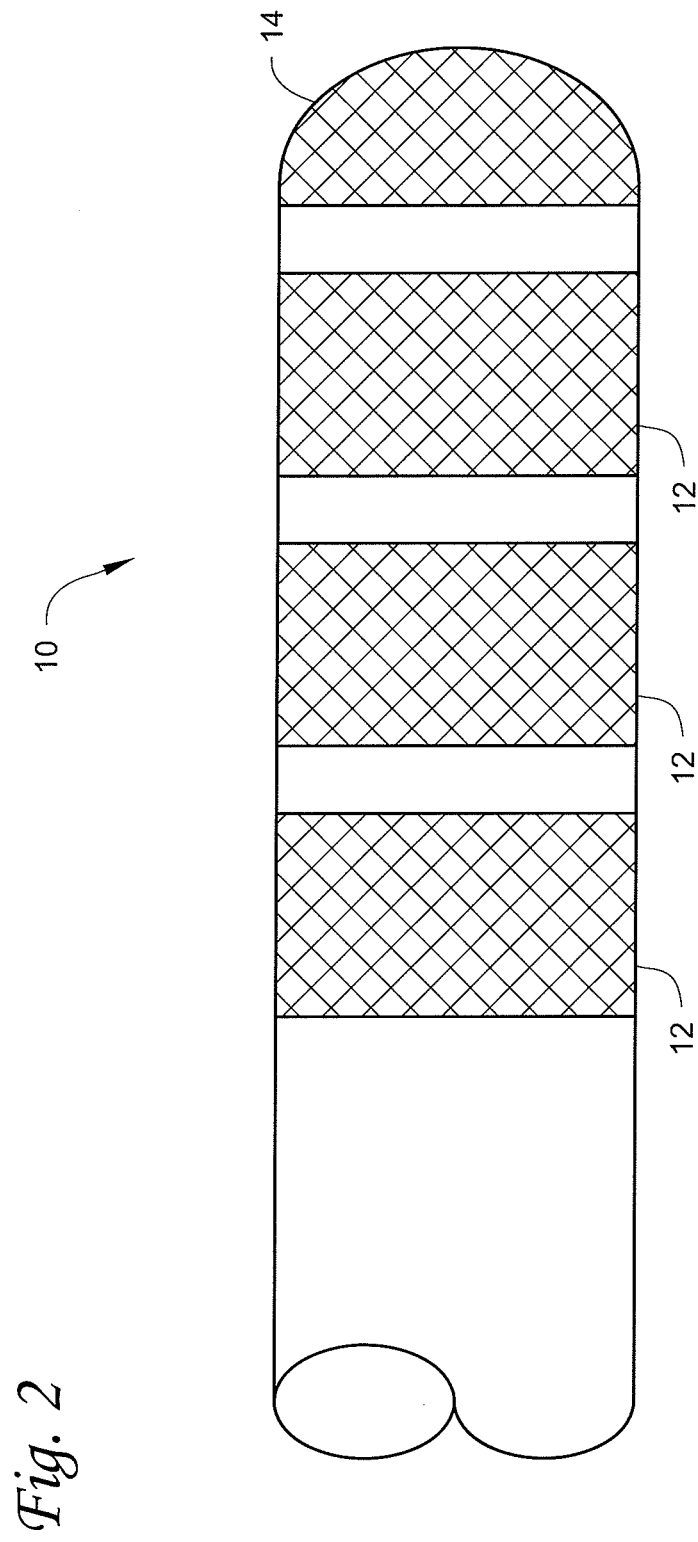
FIG. 2 depicts a partial side view of the catheter depicted in FIG. 1.

FIG. 2 depicts a partial side view of the catheter 10 as shown in FIG. 1. In this embodiment, the distal tip electrode 14 may have a length of, e.g., about 1.5 mm, the distal electrodes 12 may have a length of, e.g., about 2 mm, and the electrodes 12, 14 may be spaced apart by, e.g., about 1 mm. In other embodiments, however, the distal tip electrode 14 may have a length of, e.g., about 0.5 mm to, e.g., about 4 mm, the distal electrodes 12 may have a length of, e.g., about 0.5 mm to, e.g., about 5 mm, and the electrodes 12, 14, 16 may be spaced apart by about 0.25 mm to about 1.5 mm. Further, the distal electrodes 12 may each have a different length.

Figure 3:
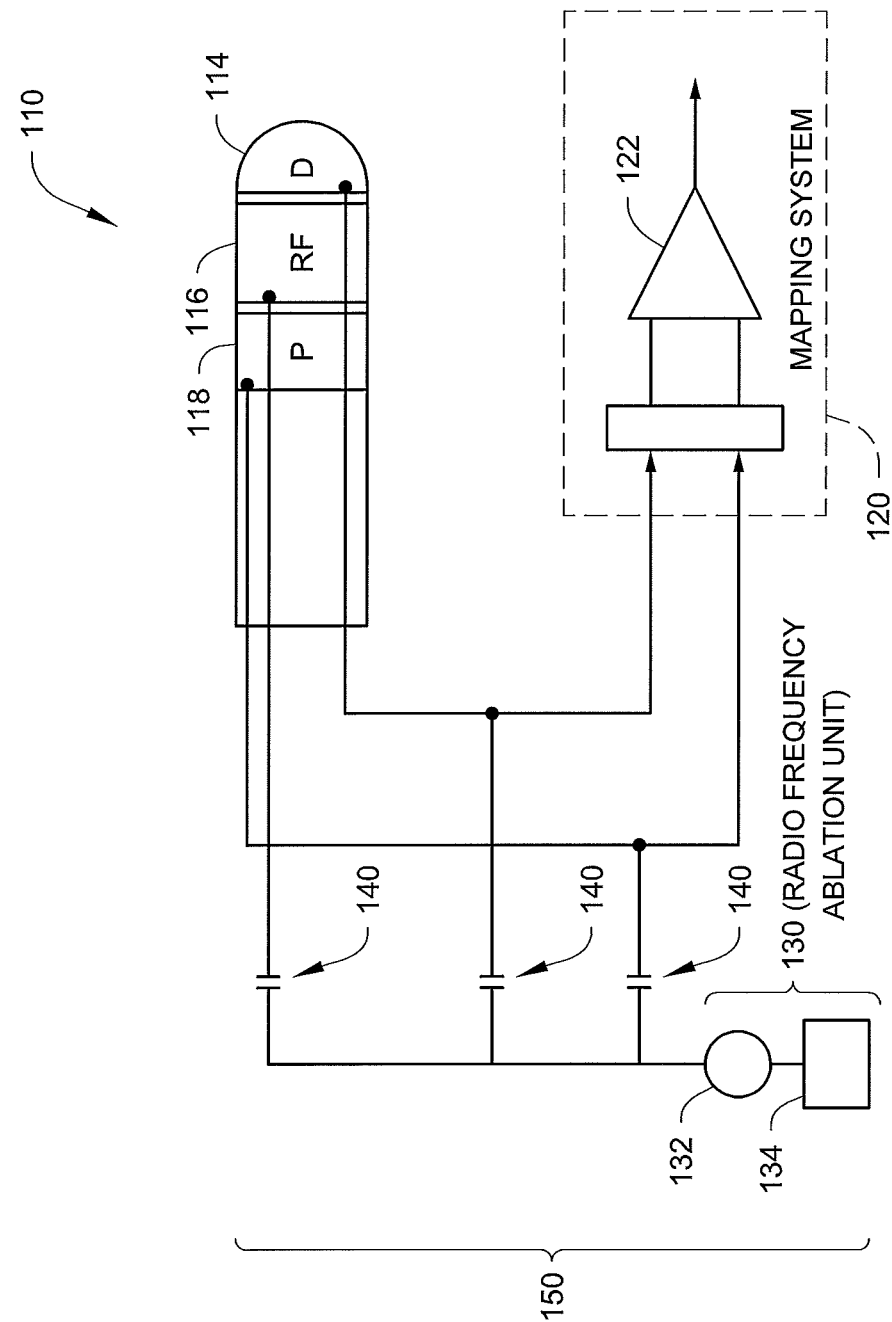
FIG. 3 depicts a schematic diagram of another exemplary embodiment of a mapping and ablation catheter system as described herein.

FIG. 3 depicts a schematic diagram of another exemplary embodiment of a mapping and ablation catheter system 150. The system may include a catheter 110, a mapping system 120, a radio frequency ablation unit 130, and capacitive components 140.

The catheter 110 may include mapping tip electrode 114, RF ablation electrode 116, and mapping electrode 118. In this embodiment, the mapping tip electrode 114 may have a length of, e.g., about 2 mm, the RF ablation electrode 116 may have a length of, e.g., about 3 mm, and the mapping electrode 118 may have a length of, e.g., about 2 mm. In other embodiments, however, the electrodes 114, 116, and 118 may have lengths of, e.g., about 0.5 mm to, e.g., about 5 mm. Further, in this embodiment, the electrodes 114, 116, 118 are spaced apart by, e.g., about 0.5 mm to about 1 mm. In other embodiments, however, the electrodes 114, 116, 118 may be spaced apart by, e.g., about 0.25 mm to, e.g., about 1.5 mm.

In this embodiment, the mapping tip electrode 114 and the mapping electrode 118 are electrically coupled to the mapping system 120. The mapping tip electrode 114 and the mapping electrode 118 may be used during mapping of, e.g., a cardiac chamber. The mapping system 120 may include electronic components, e.g., amplifier 122, to measure, amplify, etc. the signal received from the mapping electrodes 114, 118 to generate mapping data, e.g., an electrogram. The mapping system 120 may be capable of sensing electromagnetic energy in the frequency of, e.g., about 0.05 hertz to, e.g., about 500 hertz.

Each electrode 114, 116, 118 may be electrically coupled to a capacitive component 140. The capacitive components 140, in turn, may be coupled to the radio frequency ablation unit 130 in parallel. As such, the electrodes 114, 116, 118 are electrically coupled to each other via the capacitive components 140. In this embodiment, the capacitance of each capacitive component 140 may be, e.g., about 0.022 microfarads. In other embodiments, however, the capacitance of each capacitive component may be, e.g., about 0.001 microfarads to, e.g., about 0.1 microfarads.

The radio frequency ablation unit 130 may include a radio frequency generator 132 and a return patch electrode 134 (or other current return mechanism). In this embodiment, the radio frequency generator 132 may be capable of outputting electromagnetic energy in the frequency of, e.g., about 500 kilohertz. In other embodiments, however, the radio frequency ablation generator may be capable of outputting electromagnetic energy in the frequency of, e.g., about 300 kilohertz to, e.g., about 3 megahertz. A return patch electrode 134 may be attached to the patient's skin during mapping and ablation.

The capacitive components 140 offer a high impedance at low frequencies (e.g., below 500 hertz). The high impedance of the capacitive components 140 may effectively disconnect the electrodes 114, 116, 118 from each other and from the radio frequency ablation unit 130 at frequencies below 500 hertz. As such, when the radio frequency ablation unit is not providing RF energy at frequencies above, e.g., about 500 hertz, the electrodes 114, 116, 118 will be preferably effectively disconnected from each other and from the radio frequency ablation unit 130.

When, however, the radio frequency ablation unit 130 is outputting electromagnetic energy at a frequency of, e.g., about 300 kilohertz or higher, the capacitive components 140 may, in effect, behave like a near-short-circuit, thereby connecting the electrodes 114, 116, 118 in parallel and producing a large effective electrode with respect to the return patch 134.

For example, a capacitive component 140 with a value of, e.g., about 0.022 microfarads yields an impedance at 500 kilohertz of 15 ohms, which is sufficiently small such that it may not substantially reduce an ablation current. At 500 hertz, however, the same 0.022 microfarad capacitive component 140 presents an impedance of 15 kilo-ohms, which may constitute a small load seen by an input state of the amplifier 122 of the mapping system 120.

Figure 4:
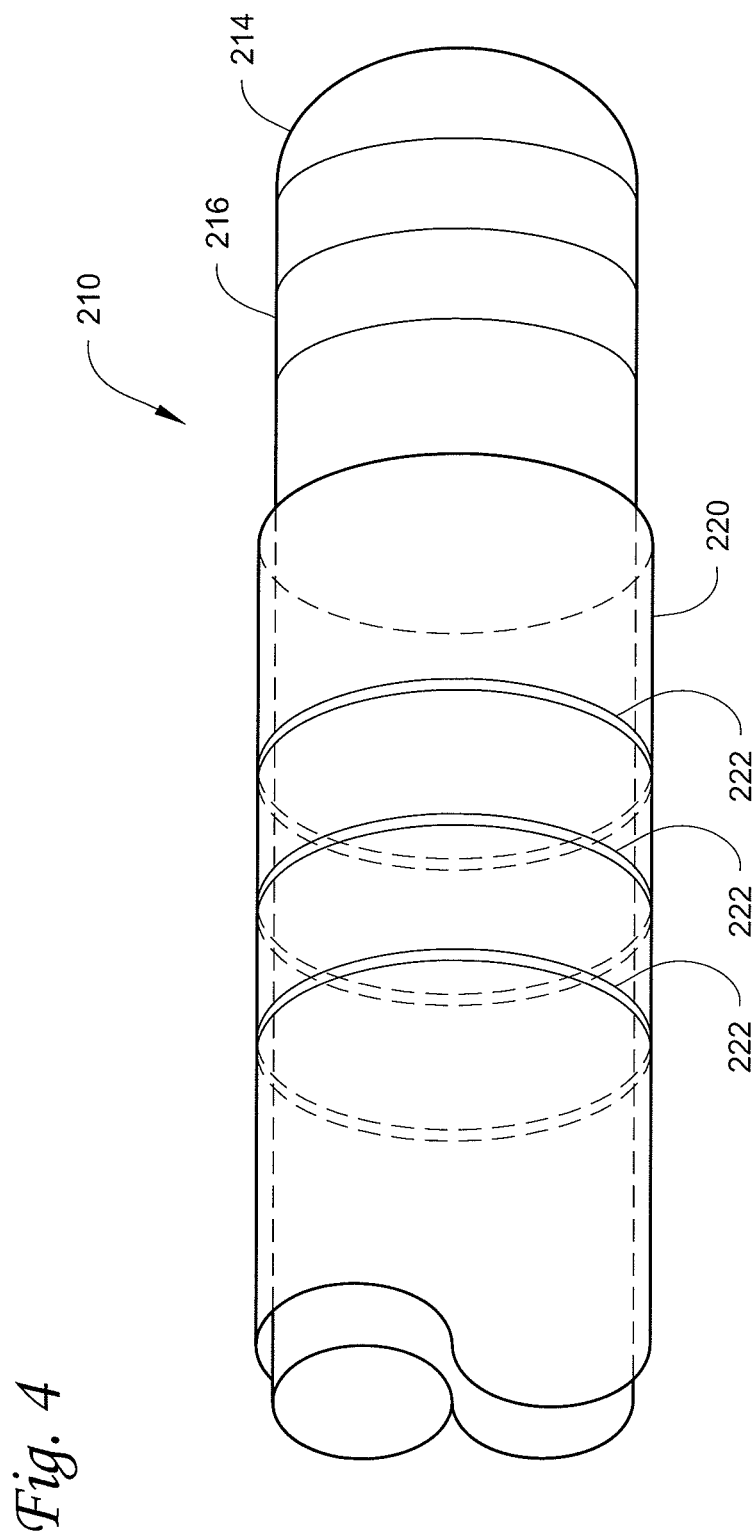
FIG. 4 depicts a partial side view of another exemplary embodiment of a mapping and ablation catheter as described herein.

FIG. 4 depicts a partial side view of another embodiment of a mapping and ablation catheter 210. In this embodiment, the catheter 210 may include a tip electrode 214, one or more catheter electrodes 216, and a sheath 220 adapted to move over the surface of the catheter 210. In this embodiment, the mapping/ablation tip of the catheter 210 may have a length of, e.g., about 10 mm. In other embodiments, however, the mapping/ablation tip may have a length of, e.g., about 1 mm to, e.g., about 20 mm.

The sheath 220 may preferably be a flexible, thin insulating sheath. The sheath 220 may be irrigated to minimize clot formation (e.g., keeping the end of the catheter 210 and/or sheath 220 relatively free of any clotting). Further, the sheath may include sheath electrodes 222 that may be used during mapping.

The sheath 220 may preferably slide back and forth (proximally and distally) along the mapping/ablation tip of the catheter 210. It may further be preferred that the sheath 220 can be fixed and/or locked at different intervals to expose more or less of the mapping/ablation tip of the catheter 210. For example, during mapping, the sheath 220 may be moved forward (advanced distally) relative to the catheter 210 and locked into position to expose 2 mm of the tip 214 (e.g., to provide a precise mapping tip). To prepare for ablation, the catheter 210 may be held in place while the sheath 220 is pulled back (moved proximally) and locked into a variety of positions exposing, e.g., 5 mm, 6 mm, or 8 mm of the tip of the catheter 210, which may produce an ablation tip of variable length.

The portion of the catheter located between two of the electrodes (e.g., mapping electrodes) may be in the form of an irrigation ring that includes one or more irrigation ports. Any such irrigation ring may preferably be connected to a lumen that extends towards the proximal end of the catheter, with the lumen being used to supply irrigation fluid to the irrigation ring. Such an irrigation ring can potentially function as an insulator to distinguish the two separated electrodes during mapping, while the same two electrodes could potentially also be used for ablation in the presence of a suitable irrigation fluid.

In some embodiments, the systems may further include one or more temperature sensors. For example, one or more temperature sensors may be provided in connection with two or more of the electrodes to provide temperature information during, e.g., testing and/or use of the ablation functions. Monitoring temperature during ablation may potentially assist the user in reducing the likelihood of coagulum development on, e.g., the ablation electrode or electrodes.

Further, in some embodiments, it may be helpful to provide two or more temperature sensors located along the catheter, with a first temperature sensor located proximate a position on the catheter where the most ablation energy is delivered and one or more additional temperature sensors spaced apart from the first temperature sensor. Using two or more temperature sensors may provide the ability to monitor a temperature gradient between the temperature sensors during and/or after ablation. In some instances, the temperature sensors may be monitored to reduce the likelihood of coagulum formation and/or improve the likelihood of lesion creation.

The complete disclosure of the patents, patent documents, and publications cited in the Background, the Summary, the Detailed Description of Exemplary Embodiments, and elsewhere herein are incorporated by reference in their entirety as if each were individually incorporated. Exemplary embodiments of some systems are described above. Those skilled in the art will recognize that many embodiments are possible within the scope of the disclosure. Other variations, modifications, and combinations of the various components and methods described herein can certainly be made and still fall within the scope of the disclosure. Thus, the invention is limited only by the following claims and equivalents thereto.

The invention claimed is:

1. A cardiac mapping and ablation catheter system comprising:
 a radio frequency ablation source comprising an output;
 a mapping device;
 a catheter comprising three or more catheter electrodes arranged along a length of the catheter, wherein the three or more catheter electrodes are spaced apart from each other along the length of the catheter, wherein two of the three or more catheter electrodes are electrically coupled to the mapping device, and wherein one catheter electrode of the three or more catheter electrodes is not electrically coupled to the mapping device; and
 a plurality of capacitive components, wherein all of the three or more catheter electrodes are electrically coupled to the output of the radio frequency ablation source through a capacitive component of the plurality of capacitive components such that energy delivered to each capacitive component by the radio frequency ablation source passes through the plurality of capacitive components to all of the three or more catheter electrodes.

2. The system of claim 1, the system further comprising a sheath capable of partially surrounding the catheter and sliding along the catheter to selectively expose one or more of the three or more catheter electrodes.

3. The system of claim 2, wherein the sheath comprises one or more sheath electrodes located on an exterior surface of the sheath, wherein the one or more sheath electrodes are electrically coupled to the mapping device.

4. The system of claim 1, wherein the capacitance of each capacitive component is 0.001 microfarads to 0.1 microfarads.

5. The system of claim 1, wherein the capacitive components electrically isolate the radio frequency ablation source from the three or more catheter electrodes when the radio frequency ablation source is disabled.

6. The system of claim 1, wherein the radio frequency ablation source is capable of outputting electromagnetic energy at a frequency of about 300 kilohertz or higher.

7. The system of claim 1, wherein the mapping device is capable of sensing electromagnetic energy in the frequency of about 500 hertz or lower.

8. The system of claim 1, wherein each of the three or more catheter electrodes is 0.5 millimeters long to 4 millimeters long.

9. The system of claim 1, wherein the three or more catheter electrodes are spaced apart from each other by 0.5 millimeters to 1 millimeter.

10. The system of claim 1, wherein one of the three or more catheter electrodes is located on a distal end of the catheter.

11. The system of claim 1, further comprising:
a sheath capable of partially surrounding the catheter and sliding along the catheter to selectively expose one or more of the three or more catheter electrodes;
one or more sheath electrodes located on an exterior surface of the sheath, wherein the one or more sheath electrodes are electrically coupled to the mapping device;
wherein the capacitance of each capacitive component is 0.001 microfarads to 0.1 microfarads; and
wherein the capacitive components electrically isolate the radio frequency ablation source from the three or more catheter electrodes when the radio frequency ablation source is disabled.

12. The system of claim 11, wherein the radio frequency ablation source is capable of outputting electromagnetic energy at a frequency of about 300 kilohertz or higher.

13. The system of claim 11, wherein the mapping device is capable of sensing electromagnetic energy in the frequency of about 500 hertz or lower.

14. The system of claim 11, wherein the radio frequency ablation source is capable of outputting electromagnetic energy at a frequency of about 300 kilohertz or higher, and wherein the mapping device is capable of sensing electromagnetic energy in the frequency of about 500 hertz or lower.

15. The system of claim 1, wherein one catheter electrode of the two catheter electrodes electrically coupled to the mapping device is located on a distal end of the catheter.

16. The system of claim 1, wherein the catheter electrode that is not electrically coupled to the mapping device is located between the two catheter electrodes electrically coupled to the mapping device.

17. The system of claim 1, wherein the catheter electrode that is not electrically coupled to the mapping device is located between the two catheter electrodes electrically coupled to the mapping device, and wherein one catheter electrode of the two catheter electrodes electrically coupled to the mapping device is located on a distal end of the catheter.

18. A cardiac mapping and ablation catheter system comprising:
a radio frequency ablation source comprising an output;
a mapping device;
a catheter comprising three catheter electrodes arranged along a length of the catheter, wherein the three catheter electrodes are spaced apart from each other along the length of the catheter, and wherein two catheter electrodes of the three catheter electrodes are electrically coupled to the mapping device, and further wherein one catheter electrode of the three catheter electrodes is not electrically coupled to the mapping device; and
wherein each catheter electrode of the three catheter electrodes is electrically coupled to a capacitive component that is electrically coupled to the output of the radio frequency ablation source such that energy delivered to each catheter electrode of the three catheter electrodes passes through the capacitive component to which the catheter electrode is electrically coupled, and wherein the capacitive components electrically isolate the radio frequency ablation source from the catheter electrodes when the radio frequency ablation source is disabled;
a sheath capable of partially surrounding the catheter and sliding along the catheter to selectively expose the catheter electrodes; and
a sheath electrode located on an exterior surface of the sheath, wherein the sheath electrode is electrically coupled to the mapping device.

19. The system of claim 18, wherein the capacitance of each capacitive component is 0.001 microfarads to 0.1 microfarads.

20. The system of claim 18, wherein the radio frequency ablation source is capable of outputting electromagnetic energy at a frequency of about 300 kilohertz or higher.

21. The system of claim 18, wherein the mapping device is capable of sensing electromagnetic energy in the frequency of about 500 hertz or lower.

22. The system of claim 18, wherein the catheter electrode electrodes are 0.5 millimeters long to 4 millimeters long.

23. The system of claim 18, wherein the catheter electrodes are spaced apart from each other by 0.5 millimeters to 1 millimeter.

24. The system of claim 18, wherein one catheter electrode of the two catheter electrodes electrically coupled to the mapping device is located on a distal end of the catheter.

25. The system of claim 18, wherein the one catheter electrode that is not electrically coupled to the mapping device is located between the two catheter electrodes electrically coupled to the mapping device.

26. The system of claim 18, wherein the catheter electrode that is not electrically coupled to the mapping device is located between the two catheter electrodes electrically coupled to the mapping device, and wherein one catheter electrode of the two catheter electrodes electrically coupled to the mapping device is located on a distal end of the catheter.

* * * * *